(12) United States Patent
Zhang et al.

(10) Patent No.: US 9,695,483 B2
(45) Date of Patent: Jul. 4, 2017

(54) METHOD OF DETERMINING HPV INTEGRATION SITE IN GENOME OF HUMAN TISSUE SAMPLE, SYSTEM AND USE THEREOF

(71) Applicant: BGI Biotechnology (Wuhan) Co., Ltd., Hubei (CN)

(72) Inventors: Yong Zhang, Guangdong (CN); Zhixiang Yan, Guangdong (CN); Lijin You, Guangdong (CN); Lichao Cao, Guangdong (CN); Ping Xiao, Guangdong (CN)

(73) Assignee: BGI Biotechnology (Wuhan) Co., Ltd., Wuhan, Hubei (CN)

( * ) Notice: Subject to any disclaimer, the term of this patent is extended or adjusted under 35 U.S.C. 154(b) by 233 days.

(21) Appl. No.: 14/331,763

(22) Filed: Jul. 15, 2014

(65) Prior Publication Data

US 2015/0024946 A1 Jan. 22, 2015

(30) Foreign Application Priority Data

Jul. 16, 2013 (CN) .......................... 2013 1 0298258

(51) Int. Cl.
*C12Q 1/70* (2006.01)
*C12Q 1/68* (2006.01)

(52) U.S. Cl.
CPC ........... *C12Q 1/708* (2013.01); *C12Q 1/6886* (2013.01); *C12Q 2600/156* (2013.01)

(58) Field of Classification Search
None
See application file for complete search history.

(56) References Cited

FOREIGN PATENT DOCUMENTS

CN 1995384 A 7/2007

OTHER PUBLICATIONS

Thorland et al. Human papillomavirus type 16 integrations in cervical tumors frequently occur in common fragile sites. Cancer Res. (2000) vol. 60, pp. 5916-5921.*
Ragin et al. Mapping and analysis of HPV16 integration sites in a head and neck cancer cell line. Int. J. Cancer (2004) vol. 110, pp. 701-709.*
Zheng Hu "Identification of high-risk Papillomavirus Integration sites and the potential Mechanism Research," Dissertation submitted to Huazhong University of Science and Technology, Apr. 2012, pp. 22-23 and 30.

* cited by examiner

*Primary Examiner* — David Thomas
(74) *Attorney, Agent, or Firm* — Lee & Hayes, PLLC

(57) ABSTRACT

Disclosed are a method of determining an HPV integration site in a genome of a human tissue sample and a system thereof. The method comprises: subjecting genome DNA of the human tissue sample to a first sequencing, to obtain a sequencing result; determining DNA fragments containing both HPV sequence and human genome sequence, based on the sequencing result; determining a pair of amplification primers based on the DNA fragments containing both HPV sequence and human genome sequence, subjecting the genome DNA of the human tissue sample to PCR amplification using the pair of amplification primers, to obtain PCR product; and subjecting the PCR product to a second sequencing, to determine the integration site in a genome of the human tissue sample. The method is easy to be operated with low cost, high efficiency and excellent repeatability, which may be used to detect all HPV genotypes one time, and may rapidly and accurately determine detailed sequence information and integration site.

10 Claims, 2 Drawing Sheets

Fig. 2
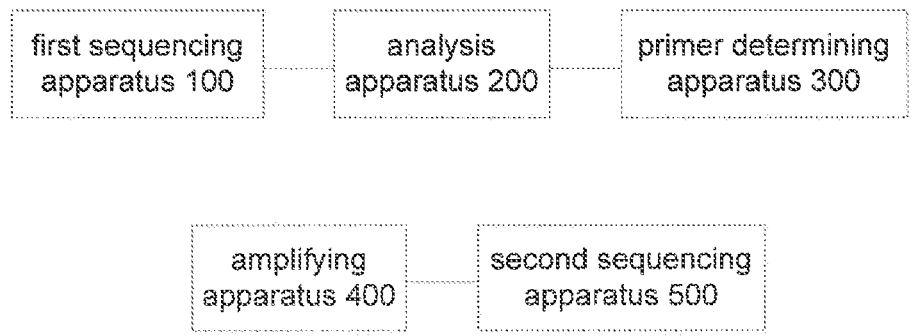
Fig. 2A
Fig. 2B
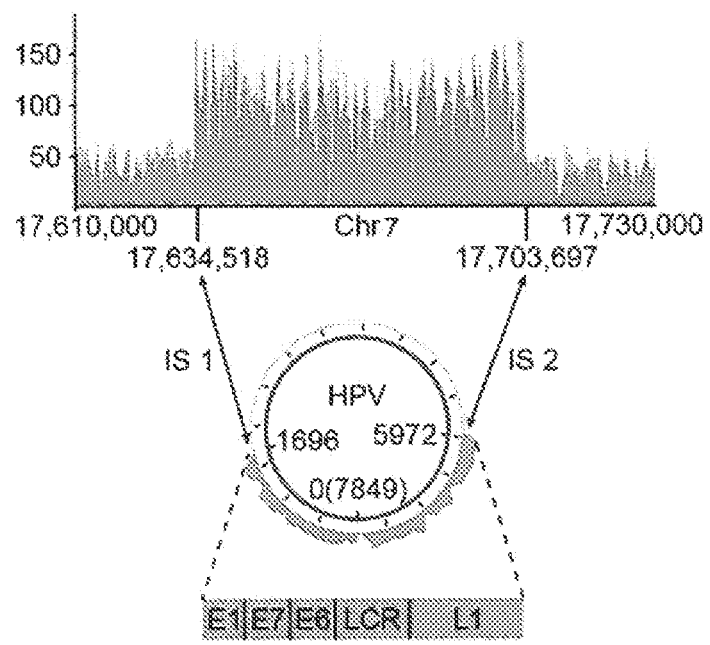
Fig. 3

SEQUENCE LISTING

<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: Primer

<400> SEQUENCE: 1
catggaagga tatgtactgc                                        20

```
<210> SEQ ID NO 2
<211> LENGTH: 18
<212> TYPE: DNA
<213> ORGANISM: Artificial
<220> FEATURE:
<223> OTHER INFORMATION: primer

<400> SEQUENCE: 2
atgttctggc tcatgtag                                                   18

<210> SEQ ID NO 3
<211> LENGTH: 1700
<212> TYPE: DNA
<213> ORGANISM: HPV

<400> SEQUENCE: 3
aatactttta acaattatac tacataaaaa agggtgtaac cgaaaacggt tgcaaccaaa     60
aacggtgcat ataaaagctt tgtggaaaag tgcattacag gatggcgcgc tttgacgatc    120
caaagcaacg accctacaag ctaccagatt tgtgcacaga attgaataca tcactacaag    180
acgtatctat tgcctgtgta tattgcaaag caacattgga acgcacagag gtatatcaat    240 ttgctttta agatttatgt atagtgtata gagactgtat agcatatgct gcatgccata    300
aatgtataga ctttttattcc agaattagag aattaagata ttattcaaac tctgtatatg    360
gagagacact ggaaaaaata actaatacag agttgtataa tttgttaata aggtgcctgc    420
ggtgccagaa accattgaac ccagcagaaa aacgtagaca ccttaaggac aaacgaagat    480
ttcacagcat agctggacag taccgagggc agtgtaatac atgttgtgac caggcacggc    540
aagaaagact tcgcagacgt agggaaacac aagtatagca ataagtatgc atggaccccg    600
ggaaacactg caagaaattg tattgcattt ggaacctcag aatgaattag atcctgttga    660
cctgttgtgt tacgagcaat taagcgagtc agaggaggaa aacgatgaag cagatggagt    720
tagtcatgca caactaccag cccgacgagc cgaaccacag cgtcacaaaa ttttgtgtgt    780
atgttgtaag tgtgacggca gaattgagct tacagtagag agctcggcag aggaccttag    840
aacactacag cagctgtttt tgagcaccct gtcctttgtg tgtccgtggt gtgcaactaa    900
ccaataatct acaatggcgg atccagaagg taccgacggg gagggaacgg ggtgtaatgg    960 ctggttctt gtagaaacaa ttgtagagaa aaaacaggg gatgtaatat cagatgatga    1020
ggatgaaact gcaacagata cagggtcgga tatggtagat tttattgaca cacaattatc    1080
catttgtgaa caggcagagc aagagacagc acaggcattg ttccatgcgc aggaagttca    1140
gaatgatgca caggtgttgc atcttttaaa acgaaagttt gcaggaggca gcaaggaaaa    1200
cagtccatta ggggagcagc taagtgtgga tacggatcta agtccacggt tacaagaaat    1260
ttcattaaat agtgggcaca aaaagcaaaa acgacggttg tttacaatat cagatagtgg    1320
ctatggctgt tctgaagtgg aagctgcaga gactcaggta actgtaaaca ctaatgcgga    1380
aaatggcggc agtgtacata gtacacaaag tagtggtggg gatagtagtg acaatgcaga    1440
aaatgtagat ccgcattgca gtattacaga actaaaggag ctattacaag caagtaacaa    1500
aaaggctgca atgctggcag tatttaaaga catatatggg ctgtcatttta cggatttggt    1560 tagaaatttt aaaagtgata aaacaacatg tacagattgg gtaatggcta tatttggagt    1620
taatccaacg gtagcagaag gctttaaaac attaattaaa ccagcaacgt tatacgccca    1680
tatccaatgt ttagattgta                                               1700

<210> SEQ ID NO 4
```

<211> LENGTH: 1888
<212> TYPE: DNA
<213> ORGANISM: HPV

<400> SEQUENCE: 4

| | | | | | |
|---|---|---|---|---|---|
| ccatttata | ataaattgga | tgatacagaa | agtgctcatg | cagctacagc | tgttattacg | 60 |
| caggatgtta | gggataatgt | gtcagttgat | tataagcaaa | cacagctgtg | tattttaggt | 120 |
| tgtgtacctg | ctattggtga | gcactgggcc | aagggcacac | tttgtaaacc | tgcacaattg | 180 |
| caacctggtg | actgtcctcc | tttggaactt | aaaaacacca | ttattgagga | tggtgatatg | 240 |
| gtggatacag | gttatggggc | aatggatttt | agtacattgc | aggatacaaa | gtgcgaggtt | 300 |
| ccattagaca | tttgtcaatc | catctgtaaa | tatccagatt | atttgcaaat | gtctgctgat | 360 |
| ccctatgggg | attctatgtt | tttttgccta | cgccgtgaac | aactgtttgc | aagacatttt | 420 |
| tggaataggg | caggtgttat | gggtgacaca | gtacctacgg | acctatatat | taaaggcact | 480 |
| agcgctaata | tgcgtgaaac | ccctggcagt | tgtgtgtatt | ccccttctcc | cagtggctct | 540 |
| attattactt | ctgattctca | attatttaat | aagccatatt | ggttacataa | ggcccagggc | 600 |
| cataacaatg | gtatttgttg | gcataatcag | ttgtttgtta | ctgtagtgga | cactacccgc | 660 |
| agtactaatt | taacattatg | tgcctctaca | caaaatcctg | tgccaagtac | atatgaccct | 720 |
| actaagttta | agcagtatag | tagacatgtg | gaggaatatg | atttacagtt | tattttttcag | 780 |
| ttgtgcacta | ttacttttaac | tgcagaggtt | atgtcatata | tccatagtat | gaatagtagt | 840 |
| atattagaaa | attggaatttt | tggtgtccct | ccaccaccta | ctacaagttt | ggtggataca | 900 |
| tatcgttttg | tgcaatcagt | tgctgttacc | tgtcaaaagg | atactacacc | tccagaaaag | 960 |
| caggatccat | atgataaatt | aaagttttgg | actgttgacc | taaaggaaaa | attttcctcc | 1020 |
| gatttggatc | aatatccct | tggtcgaaag | ttttagttc | aggctgggtt | acgtcgtagg | 1080 |
| cctaccatag | gacctcgtaa | gcgtcctgct | gcttccacgt | ctactgcatc | tactgcatct | 1140 |
| aggcctgcca | aacgtgtacg | tatacgtagt | aagaaataat | atgttagcac | atatatgtat | 1200 |
| gtttgtatgt | atggttttgt | atgttgtatg | tatgtatgta | tttgtgtgat | atattactgt | 1260 |
| atttttgtttg | tttgcgtgcg | tgtatgtatg | aatgtgccttt | gtggcatgta | tggtgttact | 1320 |
| gtacataatt | gtggtattaa | ataaagtatg | ctaatagtgt | tgtgtagggt | tgcacccttg | 1380 |
| tgagtaacaa | tactatttgt | gtgtatgtgt | attgctttgt | accctatatt | ctttcctgta | 1440 |
| tttcaagtta | taaacttgca | tactacacag | catccatttt | acttataatc | ctccattttg | 1500 |
| ctgtgcaacc | gatttcggtt | gcctgtggct | tatatgtgac | cttttaaaca | taatacctaa | 1560 |
| actggcacat | ttacaacccc | tacatagttt | aacctactgg | cgcgccttct | tggcgtacat | 1620 |
| gtggcacacc | tggtattagt | catttttcctg | tccaggtgta | ctaaaacaat | ggcttgcaca | 1680 |
| actgtatcca | caccctatgt | aataaaactg | cttttaggca | catattttag | tctgttttta | 1740 |
| cctgtgctaa | ttgtataatt | ggcgtgtaga | accactttct | tatccaacaa | tctgtctact | 1800 |
| tgttacataa | actataaact | gactcactta | tacatacata | gtttatgcaa | ccgaaaaagg | 1860 |
| ttgggcccta | taacacatac | cttttcctt | | | 1888 |

METHOD OF DETERMINING HPV INTEGRATION SITE IN GENOME OF HUMAN TISSUE SAMPLE, SYSTEM AND USE THEREOF

SEQUENCE LISTING INFORMATION

A computer readable textfile, entitled "10023427-0001-Sequence Listing.txt", created on or about Jul. 21, 2014, with a file size of about 5.21 KB, contains the sequence listing for this application and is hereby incorporated by reference in its entirety.

REFERENCE TO EARLIER APPLICATIONS

This application claims the benefit of Chinese Application No. 201310298258.X, filed Jul. 16, 2013, which is hereby expressly incorporated by reference in its entirety.

TECHNICAL FIELD

Embodiments of the present disclosure generally relate to a method of determining an HPV integration site in a genome of a human tissue sample and a system thereof.

BACKGROUND

Human papillomavirus (abbreviated as HPV) is one closed circular deoxyribonucleotide virus, of which 118 kinds of subtypes have been found, in which 5, 6, 8, 11, 16, 18, 31, 33 and etc genotypes of virus subtypes are associated with human malignancy. Viral oncogenes (such as E6 and E7) carrying thereof will integrate into host genome along with viral DNA during the early development of carcinoma, which results in expression changes of these two oncogenes (such as E6 and E7). Proteins p53 and pRB respectively encoded by E6 and E7 accelerate degradation of host cell, which greatly contributes to carcinogenicity of HR-HPV. Mechanism of replication and separation during chromosome mitosis interfered by such two oncoproteins, induces sever instability of chromosome. It has been verified by researches that integration of high risk HPV DNA relates to changes of chromosome amount and structure. Mice experiment verifies that papilloma virus induce tumorigensis by disrupting DNA sequence not only through viral oncogene but also via integrating host genome. Therefore, integration of HR-HPV results in enhancements of cell immortalization, uncontrollable proliferation and cell instability. Studying on integration of HPV viral gene is benefit to determine pathologic evolution of infection cells by clinical doctors, predicting that whether the infection cells produce viral damage and apoptosis in general or cacinogenesis step by step. In addition, determination of the integration site is also benefit to re drug target research.

Traditional methods of determining HPV genotype use chip genotyping method and mass spectrometry genotyping, which can only determine HPV genotype, other than HPV integration site.

So far, traditional methods detect viral integration site using target or signal amplification method. However, these methods only detect one kind of HPV genotype one time, or have other technical disadvantages, for example, signal detection problem of hybridization in situ and severity conditions of PCR analysis, which are both disadvantage to detect complex integration. The above traditional methods not only are time-consuming and laborious, but also have difficulties in finding new integration sites.

Therefore, currently the method of determining an HPV integration site in a genome of a human tissue sample still needs to be improved.

SUMMARY

Embodiments of the present disclosure seek to solve at least one of the problems existing in the related art to at least some extent. Thus, one purpose of the present disclosure is to provide a method of determining an HPV integration site in a genome of a human tissue sample, which may accurately obtain detailed sequence information and integration site, by which may detect all HPV genotypes one time.

Embodiments of a first broad aspect of the present disclosure provide a method of determining an HPV integration site in a genome of a human tissue sample. According to embodiments of the present disclosure, the method may comprise: subjecting genome DNA of the human tissue sample to a first sequencing, to obtain a sequencing result; determining DNA fragments containing both HPV sequence and human genome sequence, based on the sequencing result; determining a pair of amplification primers based on the DNA fragments containing both HPV sequence and human genome sequence, subjecting the genome DNA of the human tissue sample to PCR amplification using the pair of amplification primers, to obtain PCR product; and subjecting the PCR product to a second sequencing, to determine the integration site in a genome of the human tissue sample.

Inventors of the present disclosure surprisingly that the method of determining an HPV integration site in a genome of a human tissue sample according to embodiments of the present disclosure, is easy to be operate with low cost, high efficiency and good repeatability. According to embodiments of the present disclosure, the method of determining an HPV integration site in a genome of a human tissue sample may be used to detect all HPV genotypes one time, which may rapidly and accurately determine specific sequence information and integration site, so as to provide rapid, high-efficient and accurate technical support for clinical research and application.

Embodiments of a second broad aspect of the present disclosure provide a system for determining an HPV integration site in a genome of a human tissue sample. According to embodiments of the present disclosure, the system may comprise: a first sequencing apparatus, for subjecting genome DNA of the human tissue sample to a first sequencing, to obtain a sequencing result; an analysis apparatus, connected to the first sequencing apparatus, for determining DNA fragments containing both HPV sequence and human genome sequence, based on the sequencing result; a primer determining apparatus, connected to the analysis apparatus, for determining a pair of amplification primers based on the DNA fragments containing both HPV sequence and human genome sequence; an amplifying apparatus, configured with the pair of amplification primers, for subjecting the genome DNA of the human tissue sample to PCR amplification using the pair of amplification primers, to obtain PCR product; and a second sequencing apparatus, connected to the amplifying apparatus, for subjecting the PCR product to a second sequencing, to determine the integration site in a genome of the human tissue sample.

According to embodiments of the present disclosure, the system for determining an HPV integration site in a genome of a human tissue sample, having a simple construction, is easy to be prepared and operated with low cost for production and usage, which is suitable for implementing the method of determining an HPV integration site in a genome of a human tissue sample with high efficiency and excellent repeatability. The inventors surprisingly find out that the system for determining an HPV integration site in a genome of a human tissue sample may be used to detect all HPV genotypes one time, which may rapidly and accurately determine detailed sequence information and integration site, so as to provide a rapid, high-efficient and accurate technical platform for clinical research and application.

Embodiments of a third broad aspect of the present disclosure provide a method of monitoring development or prognosis of a disease comprising: determining an HPV integration site in a genome of a human tissue sample. In another word, there is provided use of the method or the system above mentioned in monitoring development and prognosis of a disease. According to embodiments of the present disclosure, the disease is induced by HPV infection.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference the accompanying drawings, in which:

FIG. 2 is a schematic diagram showing a system for determining an HPV integration site in a genome of a human tissue sample and parts thereof according to an embodiment of the present disclosure, in which:

FIG. 2A is a schematic diagram showing a system for determining an HPV integration site in a genome of a human tissue sample according to an embodiment of the present disclosure, FIG. 2B is a schematic diagram showing an analysis apparatus according to an embodiment of the present disclosure;

FIG. 3 is an image showing an example of determined HPV integration site and integration fragment in a genome of a human tissue sample according to an embodiment of the present disclosure.

DETAILED DESCRIPTION

Figure 1:
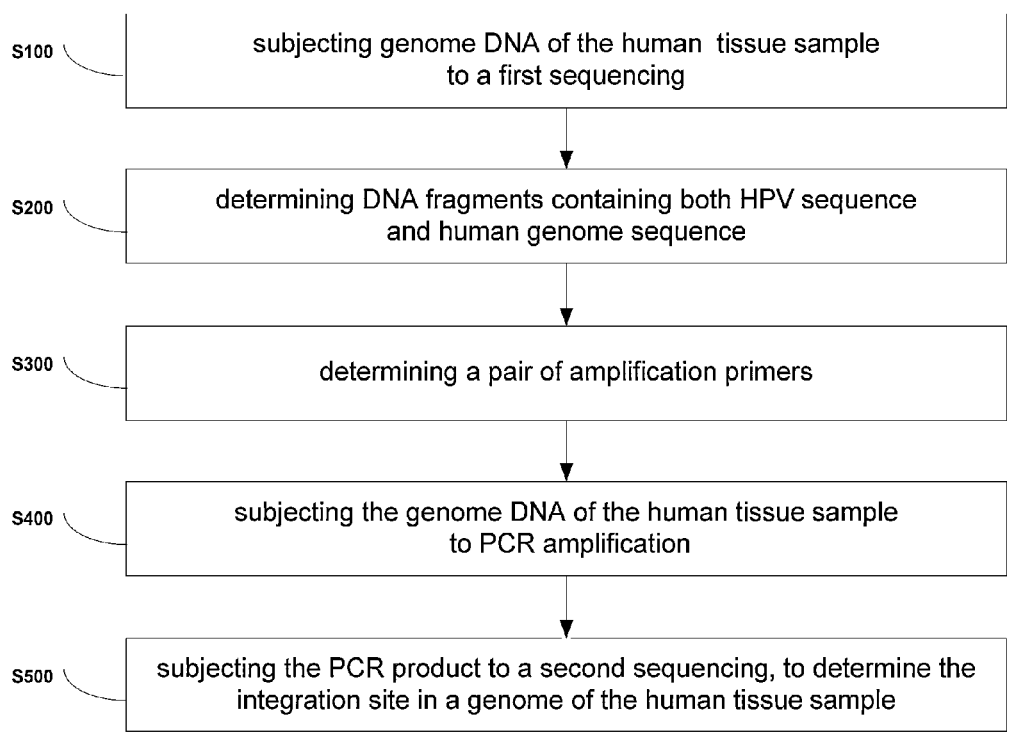
FIG. 1 is a flow chart showing method of determining an HPV integration site in a genome of a human tissue sample according to an embodiment of the present disclosure.

Reference will be made in detail to embodiments of the present disclosure. The embodiments described herein with reference to drawings are explanatory, illustrative, and used to generally understand the present disclosure. The embodiments shall not be construed to limit the present disclosure. The same or similar elements and the elements having same or similar functions are denoted by like reference numerals throughout the descriptions.

Method of Determining an HPV Integration Site in a Genome of a Human Tissue Sample According to one aspect of the present disclosure, there is provided a method of determining an HPV integration site in a genome of a human tissue sample. According to an embodiment of the present disclosure, referring to FIG. 1, the method may further comprise:

S100: Subjecting Genome DNA of the Human Tissue Sample to a First Sequencing, to Obtain a Sequencing Result Firstly, genome DNA of the human tissue sample is subjected to a first sequencing, to obtain a sequencing result. According to embodiments of the present disclosure, types of the human tissue sample suitable for the present disclosure are not subjected to special restrictions, according to some embodiments of the present disclosure, the human tissue sample is at least one selected from a group consisting of tissue infected with HPV, cancerous tissue and juxtacancerous tissue. According to embodiments of the present disclosure, prior to the step of subjecting genome DNA of the human tissue sample to a first sequencing, the method may further comprise a step of extracting the genome DNA from the human tissue sample.

Besides, according to embodiments of the present disclosure, methods of subjecting genome DNA of the human tissue sample to a first sequencing are not subject to special restrictions. According to some specific examples of the present disclosure, the genome DNA of the human tissue sample is subjected to the first sequencing by mean of at least one selected from a group consisting of Hiseq2000, SOLiD, 454 and single molecule sequencing technology, preferably the genome DNA of the human tissue sample is subjected to the first sequencing by mean of Hiseq2000 sequencing technology. Accordingly the sequencing has a high throughput and an accurate result, by which may effectively improve efficiency and accuracy of subsequent experiments. In addition, after the technical platform by which the genome DNA of the human tissue sample is subjected to the first sequencing is determined, a sequencing-library should be constructed with the genome DNA of the human tissue sample, and the obtained sequencing-library should be subsequently sequenced to obtain the sequencing result, in accordance with requirements for library constructing and sequencing of the determined technical platform. According to some embodiments of the present disclosure, during the step of subjecting genome DNA of the human tissue sample to a first sequencing, a sequencing-library which includes insert fragments having a length of 500 bp, a sequencing-library including insert fragments having a length of 500 bp is constructed. Accordingly, requirements for throughput and accuracy of the first sequencing may be effectively met, so as to further improve efficiency of subsequent steps.

S200: Determining DNA Fragments Containing Both HPV Sequence and Human Genome Sequence Secondly, based on the sequencing result, DNA fragments containing both HPV sequence and human genome sequence are determined. According to embodiments of the present disclosure, the step of determining DNA fragments containing both HPV sequence and human genome sequence may further comprise: filtering the sequencing result, to obtain a filtered sequencing result; aligning the filtered sequencing result to a reference sequence, to determine the DNA fragments containing both HPV sequence and human genome sequence, in which the reference sequence is human genome and HPV genome sequence. For example, the sequencing result is aligned to an HPV standard database, to determine an HPV genotype and determine fragments containing both HPV sequence and human genome sequence. Accordingly, the DNA fragments containing both HPV sequence and human genome sequence may be effectively determined which may be benefit for performing subsequent steps.

S300: Determining a Pair of Amplification Primers

Thirdly, based on the DNA fragments containing both HPV sequence and human genome sequence, the pair of amplification primers is determined. In details, based on the DNA fragments containing both HPV sequence and human genome sequence, primer design software and etc may be used in designing pairs of amplification primers for amplifying relative sequence of the integration site. According to embodiments of the present disclosure, sequence of the pair of amplification primers is not subjected to special restrictions, as long as the relative sequence of the integration site may be effectively amplified. According to some specific examples of the present disclosure, the amplification primers comprise a first amplification primer and a second amplification primer, in which the first amplification primer has a nucleotide sequence shown as SEQ ID NO:1, the second amplification primer has a nucleotide sequence shown as SEQ ID NO: 2. In details, the pair of amplification primers is that: the first amplification primer is 5'-CATGGAAGGA-TATGTACTGC-3' (SEQ ID NO: 1); the second amplification primer is 5'-ATGTTCTGGCTCATGTAG-3' (SEQ ID NO: 2). Accordingly, the relative sequence of the integrate site may be effectively amplified.

S400: Subjecting the Genome DNA of the Human Tissue Sample to PCR Amplification

Fourthly, using the pair of amplification primers, the genome DNA of the human tissue sample is subjected to PCR amplification, to obtain PCR product. According to embodiments of the present disclosure, conditions for performing PCR amplification are not subjected to special restrictions, as long as the relative sequence of the integrate site may be effectively amplified, which is suitable for subsequent step of sequencing. According to some specific examples of the present disclosure, the genome DNA of the human tissue sample is subjected to PCR amplification by following conditions:

used PCR reaction system (50 μL) comprises 40 ng of genome DNA template of the human tissue sample, 1×GC buffer, 2.5 mM dNTPs, 5 U LA Taq polymerase (Takara), 1 μM of primers (for example the pair of the amplification primers have a nucleotide sequence shown as SEQ ID NO:1-2); and condition for PCR amplification is: 94° C. for 5 min; 32 cycles of (94° C. for 50 s, 55° C. for 30 s, 72° C. for 3.5 min); and 72° C. for 10 min.

Accordingly the amplification result is excellent, and the obtained PCR product may be effectively used in the subsequent step of second sequencing.

S500: Subjecting the PCR Product to a Second Sequencing, to Determine the Integration Site in a Genome of the Human Tissue Sample Then, the PCR product is subjected to a second sequencing, to determine the integration site in a genome of the human tissue sample. In details, the PCR product is subjected to a second sequencing based on the sequencing result, by which the HPV integration site in the genome of the human tissue sample may be effectively determined. According to embodiments of the present disclosure, methods of subjecting the PCR product to a second sequencing are not subjected to special restrictions. According to some specific examples of the present disclosure, the PCR product is subjected to the second sequencing by Sanger method. Accordingly a length of fragments is obtained by sequencing, which is benefit for determining the HPV integration site of the genome of the human tissue sample.

The inventors surprisingly find out that the method of determining an HPV integration site in a genome of a human tissue sample according to embodiments of the present disclosure is easy to be operated with low cost, high efficiency and excellent repeatability. According to embodiments of the present disclosure, the method may be used in detecting all HPV genotypes one time, by which may rapidly and accurately determine detailed sequence information and integrate site, so as to further provide rapid, effective and accurate technical support for clinical research and application.

System for Determining an HPV Integration Site in a Genome of a Human Tissue Sample According to another aspect of the present disclosure, there is provided a system for determining an HPV integration site in a genome of a human tissue sample. The system is suitable for implementing the above method of determining an HPV integration site in a genome of a human tissue sample according to embodiments of the present disclosure. According to embodiments of the present, referring to FIG. 2, the system 1000 comprises: a first sequencing apparatus 100, an analysis apparatus 200, a primer determining apparatus 300, an amplifying apparatus 400 and a second sequencing apparatus 500. According to embodiments of the present disclosure, the system for determining an HPV integration site in a genome of a human tissue sample, having a simple construction, is easy to be prepared and operated with low cost for production and usage, which is suitable for implementing the method of determining an HPV integration site in a genome of a human tissue sample with high efficiency and excellent repeatability. The inventors surprisingly find out that the system for determining an HPV integration site in a genome of a human tissue sample may be used to detect all HPV genotypes one time, which may rapidly and accurately determine detailed sequence information and integration site, so as to provide a rapid, high-efficient and accurate technical platform for clinical research and application.

In details, referring to FIG. 2, the system 1000 for determining an HPV integration site in a genome of a human tissue sample according to embodiments of the present disclosure comprises:

A first sequencing apparatus 100, is suitable for subjecting genome DNA of the human tissue sample to a first sequencing, to obtain a sequencing result. According to embodiments of the present disclosure, types of the human tissue sample suitable for the present disclosure are not subjected to special restrictions, according to some embodiments of the present disclosure, the human tissue sample is at least one selected from a group consisting of tissue infected with HPV, cancerous tissue and juxtacancerous tissue. Besides, for the above human tissue sample, genome DNA needs to be obtained, to subjecting the genome DNA of human tissue sample the first sequencing. Thus, according to embodiments of the present disclosure, the system may further comprise: a DNA extracting apparatus, connected to the first sequencing apparatus 100, and configured to extract genome DNA from the from the human tissue sample prior to the step of subjecting genome DNA of the human tissue sample to a first sequencing. In addition, according to embodiments of the present disclosure, devices which may be taken as the first sequencing apparatus 100 are not subjected to special restrictions. According to some specific examples, the first sequencing apparatus 100 is at least one selected from a group consisting of Hiseq2000, SOLiD, 454 and single molecule sequencing technology, preferably is Hiseq2000 sequencing technology. Accordingly the sequencing has a high throughput and an accurate result, by which may effectively improve efficiency and accuracy of subsequent experiments. According to some embodiments of the present disclosure, preferably, during the step of subjecting genome DNA of the human tissue sample to a first sequencing, a sequencing-library including insert fragments having a length of 500 bp is constructed. Accordingly, requirements for throughput and accuracy of the first sequencing may be effectively met, so as to further improve efficiency of subsequent steps.

An analysis apparatus 200, connected to the first sequencing apparatus 100, is suitable for determining DNA fragments containing both HPV sequence and human genome sequence, based on the sequencing result. According to embodiments of the present disclosure, the analysis apparatus 200 may further comprise: a filtering unit 201 and an aligning unit 202, in which the filtering unit 201 is suitable for filtering the sequencing result to obtain a filtered sequencing result; and the aligning unit 202 is configured with a reference sequence, connected to the filtering unit, and is suitable for aligning the filtered sequencing result to a reference sequence, to determine the DNA fragments containing both HPV sequence and human genome sequence, in which the reference sequence is human genome and HPV genome sequence. For example, the filtered sequencing result is aligned to an HPV standard database, to determine an HPV genotype and determine the DNA fragments containing both HPV sequence and human genome sequence. Accordingly, DNA fragments containing both HPV sequence and human genome sequence may be accurately and effectively determined which may be benefit for performing subsequent steps.

A primer determining apparatus 300, connected to the analysis apparatus 200, is suitable for determining a pair of amplification primers based on the DNA fragments containing both HPV sequence and human genome sequence. According to some specific examples of the present disclosure, the amplification primers comprise a first amplification primer and a second amplification primer, in which the first amplification primer has a nucleotide sequence shown as SEQ ID NO: 1, the second amplification primer has a nucleotide sequence shown as SEQ ID NO: 2. In details, the pair of amplification primers is that: the first amplification primer is 5'-CATGGAAGGATATGTACTGC-3' (SEQ ID NO: 1); the second amplification primer is 5'-ATGTTCTG-GCTCATGTAG-3' (SEQ ID NO: 2). Accordingly, the relative sequence of the integrate site may be effectively amplified. Accordingly, the relative sequence of the integrate site may be effectively amplified.

An amplifying apparatus 400, configured with the pair of amplification primers, is suitable for subjecting the genome DNA of the human tissue sample to PCR amplification using the pair of amplification primers, to obtain PCR product According to embodiments of the present disclosure, conditions for performing PCR amplification are not subjected to special restrictions, as long as the relative sequence of the integrate site may be effectively amplified, which is suitable for subsequent step of sequencing. According to some specific examples of the present disclosure, PCR reaction system (50 µL) in the amplifying apparatus 400 may be: 1 µL of genome DNA template of the human tissue sample, 5.0 µL of 10×GC buffer (Takara DRR20BG), 4.0 µL of dNTPs (2.5 mM each), 1 µL of LA Taq polymerase (Takara DRR20BG); 3 µL of upstream primer, 3 µL of downstream primer (for example the pair of the amplification primers have a nucleotide sequence shown as SEQ ID NO:1-2); 33 µL of water (HPLC grade). Conditions for PCR amplification is: 94° C. for 5 min; 32 cycles of (94° C. for 50 s, 55° C. for 30 s, 72° C. for 3.5 min); and 72° C. for 10 min. Accordingly the amplification result is excellent, and the obtained PCR product may be effectively used in the subsequent step of second sequencing.

A second sequencing apparatus 500, connected to the amplifying apparatus 400, is suitable for subjecting the PCR product to a second sequencing, to determine the integration site in a genome of the human tissue sample. In details, the PCR product is subjected to a second sequencing based on the sequencing result, by which the HPV integration site in the genome of the human tissue sample may be effectively determined. According to embodiments of the present disclosure, devices which may be taken as the second sequencing apparatus 500 are not subjected to special restrictions. According to some specific examples of the present disclosure, the second sequencing apparatus 500 is Sanger sequencing platform. Accordingly a length of fragments is obtained by sequencing, which is benefit for determining the HPV integration site of the genome of the human tissue sample.

Method of Monitoring Development or Prognosis of a Disease

According to another aspect of the present disclosure, there is provided a method of monitoring development or prognosis of a disease comprising: determining an HPV integration site in a genome of a human tissue sample. In another word, there is provided use of the method or the system above mentioned in monitoring development and prognosis of a disease. Besides, the obtained site may also benefit for studying target of HPV drug.

According to embodiments of the present disclosure, the disease is induced by HPV infection.

It should not that the existing technology still cannot meets requirements for rapidly and accurately identifying HPV integration site, while through continuous exploration and research by the inventors of the present disclosure, the above new method of detecting HPV integration site based on Next-Generation sequencing technology is developed. The present disclosure effectively solves problems existing in prior art, which may not only detect all HPV genotypes one time, but also accurately obtain detailed sequence information and integration site. Besides the method of determining an HPV integration site in a genome of a human tissue sample and the system thereof according to embodiments of the present disclosure may be suitable for both complex integration and random integration. The method of determining an HPV integration site in a genome of a human tissue sample and the system thereof according to embodiments of the present disclosure have advantages that: accurate detection result, high throughput, short cycle, low cost, easy and convenient operation and etc, which may further provide effective, rapid and accurate technical platform for clinical research and application.

Reference will be made in detail to examples of the present disclosure. It would be appreciated by those skilled in the art that the following examples are explanatory, and cannot be construed to limit the scope of the present disclosure. If the specific technology or conditions are not specified in the examples, a step will be performed in accordance with the techniques or conditions described in the literature in the art (for example, referring to J. Sambrook, et al. (translated by Huang PT), Molecular Cloning: A Laboratory Manual, 3rd Ed., Science Press) or in accordance with the product instructions. If the manufacturers of reagents or instruments are not specified, the reagents or instruments may be commercially available, for example, from Illumina.

Example 1

Referring to FIG. 2, according to the method of the present disclosure, in accordance with following steps to determine an HPV integration site in a genome of a human tissue sample:

(1) Preparation of DNA Sample:

Sample information: 47-year-old, Chinese, female, no relevant medical history or family history of hereditary cancer. The major clinical symptom was abnormal vaginal bleeding for up to 6 months. Cytological examination found high squamous intraepithelial lesion (HSIL). In HC2 detection, HR-HPV infected lesion presented positive. Biopsy specimens showed postoperative squamous cell tumor tissue.

The human tissue samples (including tissue infected with HPV, cancerous tissue and juxtacancerous tissue) were collected and the genome DNA were extracted from the human tissue samples respectively, then the extracted genome DNA were subjected to purification using a standard method.

(2) Library Constructing and Sequencing:

A sequencing-library including insert fragments having a length of 500 bp was constructed using Illumina library-constructing method, of which specific operations referred to operating instruction. Then the constructed sequencing-library was subjected to paired-end sequencing using Hiseq2000 (Illumina) platform.

(3) Data Analysis:

Raw data with low quality were subjected to a filtration. In cancerous tissue, 38.1× of coverage (114.5 billion of bases) were obtained; in juxtacancerous tissue, 41.7× of coverage (125.3 billion of bases) were obtained; in tissue infected with HPV sample 38× of coverage (114.1 billion of bases) were obtained.

Short sequences in the sequencing result were aligned to human genome using SOAPaligner. More than 80% of the short sequence in each sample could be aligned to the human genome (hg18), in cancerous tissue, about 94.1% of the reference sequence was covered once, more than 90.8% of the reference sequence was covered 10 times. Sequences which could not align to the human reference sequence were aligned to HPV genome. By aligning with the HPV standard database, the HPV genotype was determined. The realigned result showed that, in cancerous tissue sample, 3,355 of sequences could be aligned to HPV genome; while in tissue infected with HPV sample, there was none of sequences aligned to the HPV genome. In cancerous tissue sample, there were 337 of sequences of which one end aligned to the HPV genome, the other end aligned to the human genome. Two integration sites were found in these sequences, which were located at chromosome 7q21. The integration site of HPV DNA had a length of about 3.5 kb.

Using the paired-end sequencing, sequence having one end aligned to the HPV genome and the other end aligned to the human genome, was regarded as an integrated DNA fragment (i.e., DNA fragment containing both HPV sequence and human genome segue), which was used in determining the integration site. Finally, the integration site was determined with the integrated fragment by PCR amplification and Sanger sequencing.

The obtained result showed that: in cancerous tissue sample, 3,355 of sequences aligned to HPV 45 genotype; in juxtacancerous tissue, 3 of sequences aligned to the HPV genotype; while there was none of sequences aligned to HPV genome. In cancerous tissue sample, there were 337 of sequences of which one end aligned to the HPV genome, the other end aligned to the human genome.

Two integration sites, IS1 and IS2, were found in these sequences (the integration site IS1 located at an absolute position of 17634518 in the human genome, the integration site IS2 located at an absolute position of 17703697 in the human genome site), which were located at chromosome 7q21, such fragment of sequence had a length of 69 kb. While being relative to the HPV genome, the above two integration sites located at one same integrated fragment, of which had a length of about 3.5 kb, specifically comprising following two sequences:

The first sequence (>hpv45_1 (start)-1700):

```
                                                      (SEQ ID NO: 3)
aatactttaacaattatactacataaaaaagggtgtaaccgaaaacggttgcaaccaaaaacggtgcatata aaagctttgtggaaaagtgcattacaggatggcgcgctttgacgatccaaagcaacgaccctacaagctacc agatttgtgcacagaattgaatacatcactacaagacgtatctattgcctgtgtatattgcaaagcaacattgga acgcacagaggtatatcaatttgcttttaaagatttatgtatagtgtatagagactgtatagcatatgctgcatgcc ataaatgtatagacttttattccagaattagagaattaagatattattcaaactctgtatatggagagacactgga aaaaataactaatacagagttgtataatttgttaataaggtgcctgcggtgccagaaaccattgaacccagca gaaaaacgtagacaccttaaggacaaacgaagatttcacagcatagctggacagtaccgagggcagtgta atacatgttgtgaccaggcacggcaagaaagacttcgcagacgtagggaaacacaagtatagcaataagt atgcatggaccccgggaaacactgcaagaaattgtattgcatttggaacctcagaatgaattagatcctgttga cctgttgtgttacgagcaattaagcgagtcagaggaggaaaacgatgaagcagatggagttagtcatgcaca actaccagcccgacgagccgaaccacagcgtcacaaaatttttgtgtgtatgttgtaagtgtgacggcagaatt gagcttacagtagagagctcggcagaggaccttagaacactacagcagctgtttttgagccttgtcctttgtg tgtccgtggtgtgcaactaaccaataatctacaatggcggatccagaaggtaccgacggggagggaacggg gtgtaatggctggttctttgtagaaacaattgtagagaaaaaaacaggggatgtaatatcagatgatgaggatg aaactgcaacagatacagggtcggatatggtagattttattgacacacaattatccatttgtgaacaggcagag caagagacagcacaggcattgttccatgcgcaggaagttcagaatgatgcacaggtgttgcatcttttaaaac gaaagtttgcaggaggcagcaaggaaaacagtccattagggg agcagctaagtgtggatacggatctaagt
```

-continued

```
ccacggttacaagaaatttcattaaatagtgggcacaaaaaagcaaaacgacggttgtttacaatatcagata gtggctatggctgttctgaagtggaagctgcagagactcaggtaactgtaaacactaatgcggaaaatggcg gcagtgtacatagtacacaaagtagtggtggggatagtagtgacaatgcagaaaatgtagatccgcattgca gtattacagaactaaaggagctattacaagcaagtaacaaaaaggctgcaatgctggcagtatttaaagaca tatatgggctgtcatttacggatttggttagaaattttaaaagtgataaaacaacatgtacagattgggtaatggct atatttggagttaatccaacggtagcagaaggctttaaaacattaattaaaccagcaacgttatacgcccatatc caatgtttagattgta,
``` which located at the HPV viral genome from the first base to the 1700$^{th}$ base.

The second sequence (>hpv45_5971-7858(end)):

(SEQ ID NO: 4)
```
ccattttataataaattggatgatacagaaagtgctcatgcagctacagctgttattacgcaggatgttagggata atgtgtcagttgattataagcaaacacagctgtgtattttaggttgtgtacctgctattggtgagcactgggccaag ggcacactttgtaaacctgcacaattgcaacctggtgactgtcctcctttggaacttaaaaacaccattattgagg atggtgatatggtggatacaggttatggggcaatggattttagtacattgcaggatacaaagtgcgaggttccat tagacatttgtcaatccatctgtaaatatccagattatttgcaaatgtctgctgatccctatggggattctatgttttttg cctacgccgtgaacaactgtttgcaagacattttttggaatagggcaggtgttatgggtgacacagtacctacgg acctatatattaaaggcactagcgctaatatgcgtgaaaccctggcagttgtgtgtattccccttctcccagtgg ctctattattacttctgattctcaattatttaataagccatattggttacataaggcccagggccataacaatggtattt gttggcataatcagttgtttgttactgtagtggacactacccgcagtactaatttaacattatgtgcctctacacaaa atcctgtgccaagtacatatgaccctactaagtttaagcagtatagtagacatgtggaggaatatgatttacagtt tattttttcagttgtgcactattactttaactgcagaggttatgtcatatatccatagtatgaatagtagtatattagaaa attggaattttggtgtccctccaccacctactacaagtttggtggatacatatcgttttgtgcaatcagttgctgttac ctgtcaaaaggatactacacctccagaaaagcaggatccatatgataaattaaagttttggactgttgacctaa aggaaaaattttcctccgatttggatcaatatccccttggtcgaaagttttttagttcaggctgggttacgtcgtaggc ctaccataggacctcgtaagcgtcctgctgcttccacgtctactgcatctactgcatctaggcctgccaaacgtgt acgtatacgtagtaagaaataatatgttagcacatatatgtatgtttgtatgtatggttttgtatgttgtatgtatgt atttgtgtgatatattactgtattttgtttgtttgcgtgcgtgtatgtatgaatgtgccttgtggcatgtatggtgttactgta cataattgtggtattaaataaagtatgctaatagtgttgtgtagggttgcacccttgtgagtaacaatactatttgtgt gtatgtgtattgctttgtaccctatattctttcctgtatttcaagttataaacttgcatactacacagcatccattttactta taatcctccattttgctgtgcaaccgatttcggttgcctgtggcttatatgtgaccttttaaacataatacctaaactg gcacatttacaacccctacatagtttaacctactggcgcgccttcttggcgtacatgtggcacacctggtattagt cattttcctgtccaggtgtactaaaacaatggcttgcacaactgtatccacaccctatgtaataaaactgcttttag gcacatattttagtctgtttttacctgtgctaattgtataattggcgtgtagaaccactttcttatccaacaatctgtcta cttgttacataaactataaactgactcacttatacatacatagtttatgcaaccgaaaaaggttgggccctataac acatacctttctctt,
``` which located at the HPV viral genome from the 5971$^{th}$ base to the 7858$^{th}$ base.

Legends of the integrated fragment and integration sites were shown in FIG. 3, i.e., in the HPV viral genome, the last nucleotide base of the above first sequence was integrated into the human genome at an absolute position of 17634518 by the integration site IS1, while the first nucleotide base of the above second sequence was integrated into the human genome at an absolute position of 17703697 by the integration site IS2. It should note that, as the cyclic structure of HPV viral genome, the above two sequences which located at an initial position and an terminating position respectively connected head-to-tail, forming a successive sequence, i.e., a sequence containing the entire integrated fragment having a length of 3.5 kb, accordingly herein called as "the two integration sites located at one same HPV DNA integrated fragment". Such integrated fragment included E1, E6, E7, LCR and L1 regions, in which E6 and E7 were oncogenes, maintaining tumor growth; while E1 and E2 were conservative among all HPV genotype, and the encoded proteins thereof were essential for HPV replication. HPV integration resulted in E2 deletion, which increased expression of E6 and E7, further leading to tumorigenesis.

(4) Determination of the Integration Site

The above high throughput data predicted that there were two suspected integration sites IS1 and IS2 (in which the integration site IS1 located at the absolute position of 17634518, and the integration site IS2 located at the absolute position of 17703697) in the cancerous tissue and these two integration sites were located at one same HPV DNA fragment.

For such suspected integration site, the inventors designed a pair of primers below, to performing verification:

```
                                                   (SEQ ID NO: 1)
Upstream primer: 5'-CATGGAAGGATATGTACTGC-3', (SEQ ID NO: 2)
Downstream primer: 5'-ATGTTCTGGCTCATGTAG-3'.
```

Then, the above pair of primers was used in PCR amplification respectively for the genome DNA of the human tissue sample, in which:

PCR amplification system (50 µL) was:

| Reagent | Volume (µL) |
|---|---|
| genome DNA template of the human tissue sample | 1 |
| 10 × GC buffer (Takara DRR20BG) | 5.0 |
| dNTPs (2.5 mM each) (Quigen) | 4 |
| LA Taq polymerase (Takara DRR20BG) | 1 |
| Primer (upstream) | 3 |
| Primer (downstream) | 3 |
| Water (HPLC grade) | 33 |
| Total volume | 50 |

PCR Amplification Condition:

94° C. for 5 min;

94° C. for 50 s
55° C. for 30 s } 32 cycles

72° C. for 3.5 min

72° C. for 10 min

Accordingly, the PCR products of the human tissue sample were effectively obtained. Then the obtained PCR products are subjected to Sanger sequencing for verification, to determine HPV integration site in a genome of a human tissue sample. The results showed that the two of the integration sites obtained in the previous step were verified to be a site which HPV integrated into a host genome.

(5) Universal Reference Data

Human genome data (hg 18) was downloaded from UCSC database (genome.ucsc.edu/), which included genes and repeat annotation. COSMIC v58 and a series of oncogenes were downloaded from sanger.ac.uk/genetics/CGP/Census/. Sequence of HPV gene was downloaded from hpv-web.lanl.gov/. dbSNP132 and data of 1000 Genomes Project were downloaded from NCBI FTP website (ncbi.nlm.nih.gov/Ftp/). Data of integration site of human disease-associated virus was obtained from scbit.org/dbmi/drvis. Sensitive sites of local human chromosome could refer to literature by Sandra etc.

Reference throughout this specification to "an embodiment", "some embodiments", "one embodiment", "another example", "an example", "a specific examples" or "some examples" means that a particular feature, structure, material, or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific examples" or "in some examples" in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

What is claimed is:

1. A method of determining an HPV integration site in a genome of a human tissue sample comprising the following steps:
   subjecting genomic DNA of the human tissue sample to a first sequencing, to obtain a sequencing result;
   determining DNA fragments containing both HPV sequence and human genomic sequence, based on the sequencing result;
   determining a pair of amplification primers based on the DNA fragments containing both HPV sequence and human genomic sequence;
   subjecting the genomic DNA of the human tissue sample to PCR amplification using the pair of amplification primers, to obtain a PCR product; and
   subjecting the PCR product to a second sequencing, to determine the integration site in a genome of the human tissue sample.

2. The method of claim 1, wherein the human tissue sample is at least one selected from a group consisting of a HPV infected tissue, a cancerous tissue, and a juxtacancerous tissue.

3. The method of claim 1, wherein prior to the step of subjecting genomic DNA of the human tissue sample to a first sequencing, the method further comprises a step of:
   extracting the genomic DNA from the human tissue sample.

4. The method of claim 1, wherein the method further comprises a step of constructing a sequencing-library comprising fragments having a length of 500 bp, during the step of subjecting genomic DNA of the human tissue sample to the first sequencing.

5. The method of claim 1, wherein the step of determining DNA fragments containing both HPV sequence and human genomic sequence further comprises:
   filtering the sequencing result, to obtain a filtered sequencing result; and
   aligning the filtered sequencing result to a reference sequence, to determine the DNA fragments containing both HPV sequence and human genomic sequence.

6. The method of claim 5, wherein the reference sequence is human genomic and HPV genomic sequence.

7. The method of claim 1, wherein the amplification primers comprise a first amplification primer and a second amplification primer, wherein the first amplification primer has a nucleotide sequence as set forth in SEQ ID NO: 1, and the second amplification primer has a nucleotide sequence as set forth in SEQ ID NO: 2.

8. The method of claim 1, the PCR product is subjected to the second sequencing by the Sanger method.

9. A method of monitoring development or prognosis of a disease comprising: determining an HPV integration site in a genome of a human tissue sample according to claim 1.

10. The method of claim 9, wherein the disease is induced by HPV infection.

* * * * *